United States Patent [19]

Grüntzig et al.

[11] 4,195,637
[45] Apr. 1, 1980

[54] CATHETER ARRANGEMENT, METHOD OF CATHETERIZATION, AND METHOD OF MANUFACTURING A DILATATION ELEMENT

[75] Inventors: Andreas Grüntzig; Hans Gleichner, both of Zürich, Switzerland

[73] Assignee: Schneider Medintag AG, Zürich, Switzerland

[21] Appl. No.: 853,190

[22] Filed: Nov. 21, 1977

[30] Foreign Application Priority Data

Oct. 21, 1977 [CH] Switzerland ............... 12835/77

[51] Int. Cl.² ........................................... A61M 25/00
[52] U.S. Cl. ................................. 128/348; 128/349 B
[58] Field of Search .................. 128/344, 438, 349 B, 128/349, 350, 351, 404, 419 P, 206 E, 205 R, 246, 208

[56] References Cited

U.S. PATENT DOCUMENTS

| | | | |
|---|---|---|---|
| 3,086,525 | 4/1963 | Whitcomb | 128/348 X |
| 3,498,286 | 3/1970 | Polanyl et al. | 128/348 |
| 3,635,223 | 1/1972 | Klieman | 128/348 |
| 3,831,588 | 8/1974 | Rindner | 128/348 X |
| 3,837,347 | 9/1974 | Tower | 128/344 X |
| 3,924,632 | 12/1975 | Cook | 128/348 |
| 3,941,119 | 3/1976 | Corrales | 128/348 X |
| 3,978,863 | 9/1976 | Fettel et al., | 128/348 |
| 4,033,331 | 7/1977 | Guss et al. | 128/348 |
| 4,057,065 | 11/1977 | Thow | 128/348 |
| 4,072,146 | 2/1978 | Howes | 128/348 |
| 4,088,135 | 5/1978 | O'Neill | 128/348 |
| 4,114,603 | 9/1978 | Wilkinson | 128/348 |

*Primary Examiner*—E. H. Eickholt
*Attorney, Agent, or Firm*—Werner W. Kleeman

[57] ABSTRACT

A catheter arrangement for opening or closing hollow spaces, cavities, passages and the like comprising a guide catheter and a dilatation catheter. A dilatation element arranged at the dilatation catheter has an at least partially cylindrical foldable wall. The catheterization technique employable with such catheter arrangement contemplates introducing the guide catheter by forces applied in translatory and rotational direction and engaging at the surface layer of the guide catheter, into the near region of the hollow space to be opened or closed, then inserting the dilatation catheter through a bore of the guide catheter, with the dilatation element having in its internal space a negative pressure in relation to the hollow space which is to be opened or closed. The dilatation catheter is then inserted through the guide catheter to such an extent that the dilatation element arrives at the loation which is to be opened or closed and at that location is dilated to a predetermined form and to the necessary diameter with a pre-selected excess pressure. There is also disclosed a method of manufacturing a dilatation element for use with the catheter arrangement.

17 Claims, 9 Drawing Figures

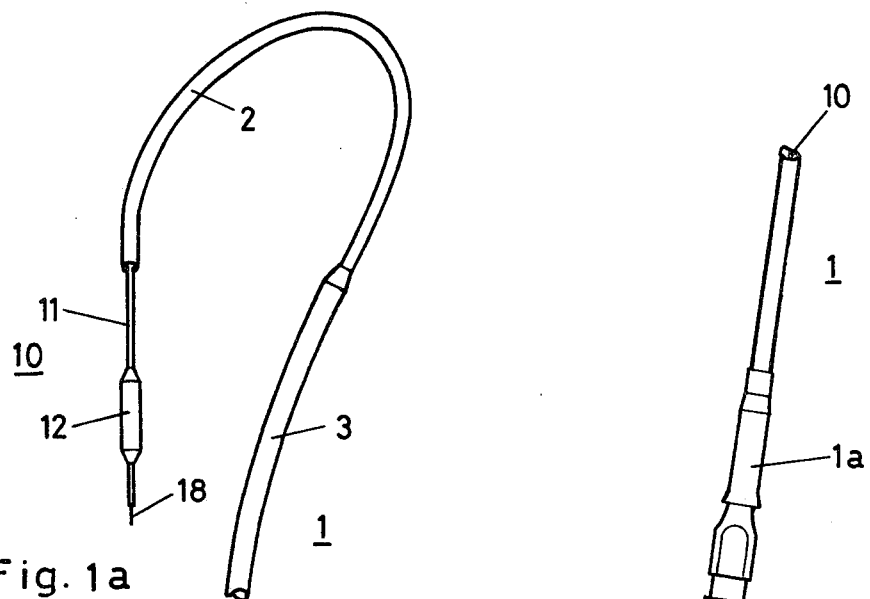
Fig. 1a
Fig. 1
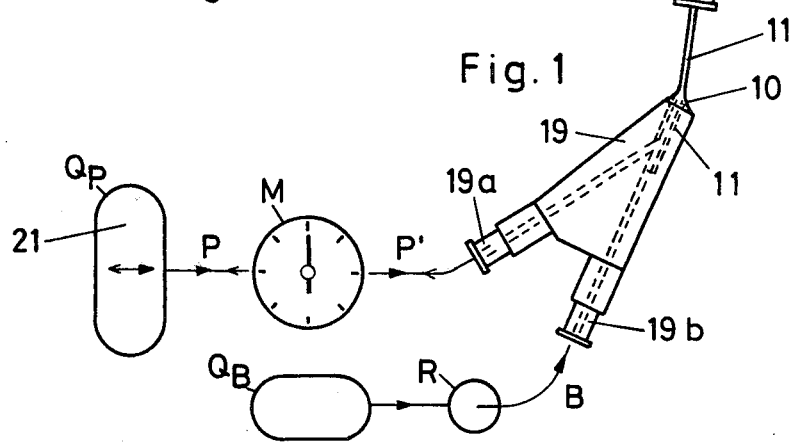
Fig. 2
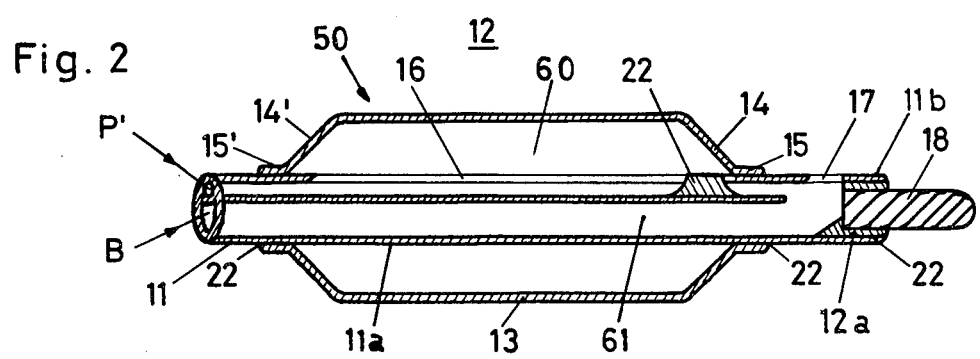

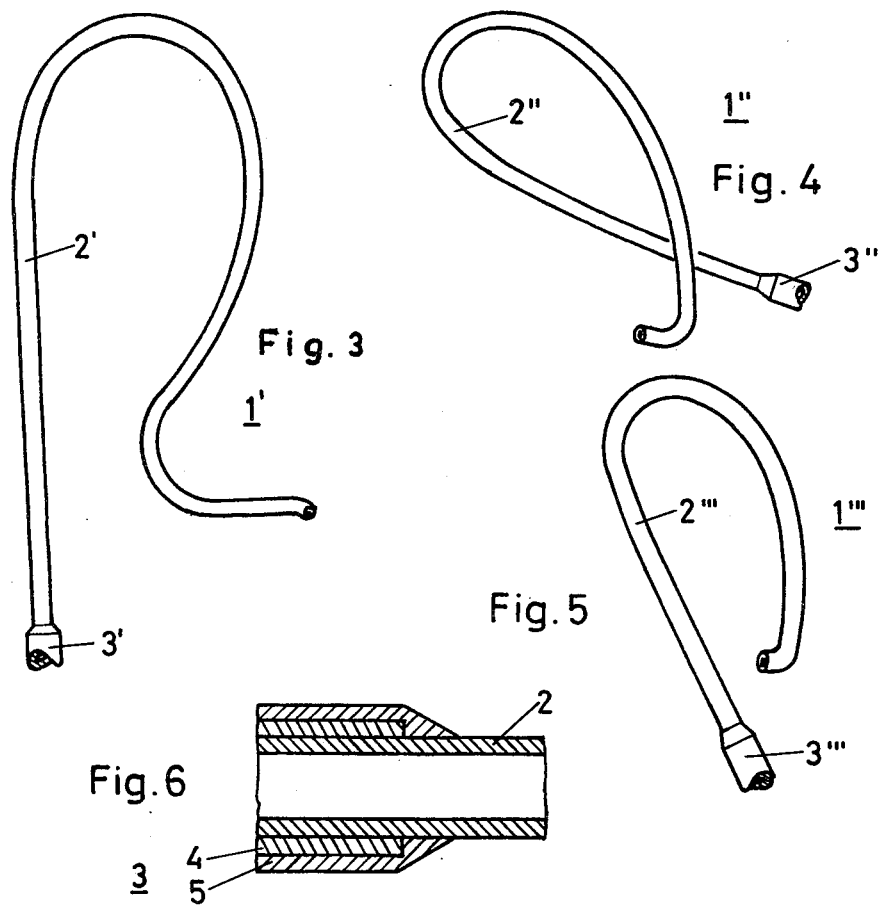
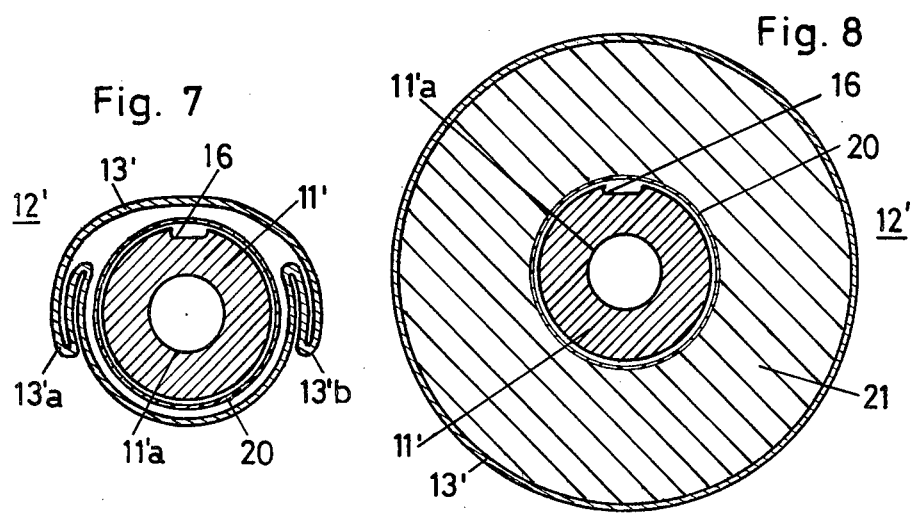

CATHETER ARRANGEMENT, METHOD OF CATHETERIZATION, AND METHOD OF MANUFACTURING A DILATATION ELEMENT

BACKGROUND OF THE INVENTION

The present invention relates to a new and improved construction of a catheter arrangement for opening or closing hollow spaces, cavities, passages and the like—hereinafter usually referred to generally as either hollow spaces or hollow cavities—which is of the type comprising a guide catheter and a dilatation catheter, and this invention furthermore relates to a method of catheterization with such catheter arrangement and to a method of manufacturing a dilatation element.

Catheters are frequently employed in technical and medical fields for opening or closing hollow spaces or cavities.

Catheters are of particular significance in internal medicine. Doctors Charles T. Dotter and Melvin P. Judkins disclosed a new technique of catheter recanalisation in stenotic or obstructed vessel sections. (Cf. Dotter, Ch. T., M.D.; Judkins, M.P., M.D.: Transluminal Treatment of Arteriosclerotic Obstruction. Circulation 30, pages 654–670, 1964)

The therein described technique of recanalization contemplates initially probing the stenotic or obstructed vessel section with a guide wire and then inserting a catheter. In this way there is formed a new lumen and the vessel continuity is again re-established. The obstructing material is neither dislocated nor removed from the vessel, merely pressed against the wall.

Based upon the previously mentioned work there have been developed spherical-shaped, balloon-like dilatation catheters which are positioned at the site of the stenosis and expanded by means of pressurized water infed through the interior of the catheter.

In practice, the heretoforeknown catheters, apart from their limited field of use, are also associated with the danger that complications arise, such as embolization of the obstructing material, bleeding and so forth.

SUMMARY OF THE INVENTION

Hence, it is a primary object of the present invention to provide a new and improved construction of catheter which enables opening occluded or at least partially obliterated, sensitive hollow spaces or cavities without mechanical damage in such a manner that the obtained openings have throughout their entire length a defined, a flow-favorable, cross-section which is accommodated to the hollow space.

Another of the objects aims at the provision of a catheter which enables reaching even extremely poorly accessible and sensitive hollow spaces or cavities and to dilate and/or close the same.

Still a further significant object of the present invention concerns the provision of a safe, simple and effective catherization method.

A further important object of the present invention is directed to a method of reliably and inexpensively fabricating a dilatation element for a catheter.

Now in order to implement these and still further objects of the invention, which will become more readily apparent as the description proceeds, the catheter of the present development is manifested by the features that a dilatation element is arranged at the dilatation catheter and such dilatation element has an at least partially cylindrical, foldable wall. A further preferred embodiment of the invention contemplates providing for the pressure system for the dilatation catheter a pressure measuring device which indicates excess pressures and negative pressures.

By connecting the dilatation catheter at a suction-pressure pump and by appropriately monitoring the pressure by means of the pressure measuring device, it is possible to carry out a stepwise dilatation, without there resulting a disturbing step formation at the vessel wall or particularly dangerous axial forces being transmitted to the vessel wall. For this purpose the dilatation catheter is always forwardly advanced in an evacuated state, i.e., the correspondingly rolled-in dilatation element does not or only slightly touches the hollow space and is only then dilated by means of a pre-determined excess pressure to a pre-determined shape and the requisite diameter at the site which is to be opened or closed.

Additionally, the pressure measuring device which is connected at the proximal end of the dilatation catheter enables utilization of the dilatation element as a measuring feeler which indicates external, mechanical pressure effects in the dilated hollow space.

Preferred embodiments of the dilatation element possess lengthwise dimensions of their walls which amount to at least twice their outer diameter. Such type elongate configured cylindrical dilatation elements produce defined openings which are favorable to flow and accommodated to the dilated hollow space.

A further construction of dilatation element as contemplated by the invention has conical-shaped terminal regions which at both sides merge into cylindrical-shaped collars and enable exact centering of the dilatation element upon a support hose.

A preferred embodiment of dilatation element is fabricated from polyvinylchloride. Such type dilatation elements preferably possess wall thicknesses in a range of 0.01 mm to 0.8 mm, and their dimensions depend upon the size of the hollow space or cavity to be dilated and upon the material to be dilated.

A further construction of a dilatation catheter has a number of hollow spaces which are closed with respect to one another and provided in its support hose, the hollow spaces are connected with the proximal end of the catheter and are open at the outer or jacket surface and/or at the distal region of the catheter. Consequently, there can be undertaken at the site of the hollow space to be dilated, for instance pressure measurements or injections and so forth.

If there is inserted at the region of the dilatation element a marking element which is impervious or only slightly pervious to radiation, preferably a gold foil, then it is possible to carry out an X-ray localization also in the evacuated state of the dilatation element.

As already alluded to above, the invention is also directed to a method of manufacturing a dilatation element formed of polyvinylchloride, wherein in a first method step a commercially available hose formed of polyvinylchloride is introduced into a prepared mold and exposed to a thermal treatment at a temperature of 80° C. to 120° C. and for a time duration of at least twenty seconds and with an internal pressure in the mold of 0.1 to 8 atmospheres excess pressure (gauge pressure), and during a second step, with constant internal pressure, cooled within at most two minutes to room temperature. Then the thus-formed dilatation element during a third method step, is fixed and sealed upon a polyethylene-containing support or carrier hose by an adhesive bond.

In order to guide the dilatation catheter to the site where it is used, there is required a guide catheter which comprises an inner hose having a surface layer extending upon its outer or jacket surface at least along a part of its length. This surface layer is capable of transmitting greater torsional forces in comparison to the inner hose.

With this arrangement the guide catheter can be manually guided from its proximal region and directed to the site where it is used.

A further advantageous constructional embodiment of the invention utilizes a guide catheter which is pre-formed at its distal region in such a manner that it possesses a mechanical pre-stress in relation to its position of use. Due to this measure the guide catheter also retains its pre-determined shape even after undertaking complicated manipulations which produce corresponding deformations.

A particularly favorable construction contemplates using a surface layer for the transmission of torsion forces which consists of a synthetic fiber fabric having a protective layer applied thereto.

The synthetic fiber fabric, preferably formed of polyamide (nylon), is directly woven at the inner hose of the guide catheter and thereafter is covered by a protective hose consisting of fluoroethylenepropylene and form shrunk under thermal action.

An embodiment of the invention which is especially suitable for medical applications contemplates constructing the guide catheter to have a maximum outside diameter of 4 mm and at its distal region an outside diameter of maximum 3.5 mm, whereas its inner diameter amounts to 1.2 to 3 mm.

The invention also is concerned with an advantageous method of catheterization with a catheter of the type previously described, wherein the guide catheter is introduced by the application of forces in translatory and rotational direction, which engage at the surface layer, into the near region of the hollow space or cavity which is to be opened or closed. Thereafter the dilatation catheter is inserted through a bore of the guide catheter, and the internal space of the dilatation element is at a negative pressure in relation to the pressure prevailing in the hollow space which is to be opened or closed. Then the dilatation catheter is introduced through the guide catheter to such an extent that the dilatation element arrives at the location which is to be opened or closed and there dilated by means of a pre-selected excess pressure to its pre-determined shape and the requisite diameter.

The novel dilatation procedure enables a recanalization of vessels also filled with a flowing liquid, especially percutaneous transluminal recanalization of chronic aterioschlerotic obstructions.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 illustrates part of a catheter arrangement having a double lumen dilatation catheter and associated schematically illustrated pressure and measuring devices;

FIG. 1a shows the distal region of the catheter arrangement or catheter depicted in FIG. 1;

FIG. 2 is a sectional view of the dilatation element of the catheter of FIG. 1;

FIG. 3 illustrates a first variant embodiment of a pre-formed guide catheter;

FIG. 4 illustrates a second variant of a preformed guide catheter;

FIG. 5 illustrates a third variant of a preformed guide catheter;

FIG. 6 illustrates the construction of the guide catheter used in the arrangement of FIG. 1;

FIG. 7 is a sectional view of a schematically illustrated dilatation element in its evacuated state; and FIG. 8 illustrates the dilatation element of FIG. 7 in its dilated state.

DETAILED DESCRIPTION OF THE PREFERRED EMBODIMENTS

Describing now the drawings, in FIGS. 1 and 1a there is shown a catheter or catheter arrangement having a guide catheter 1 into the internal or inner hose 2 of which there has been inserted a dilating or dilatation catheter 10. Guide catheter 1 comprises such inner hose 2 which is provided at its linear portion with a surface layer 3 and transforms into a channel 1a.

The dilating catheter 10 has a double lumen support or carrier hose 11, at the distal end of which there is mounted a dilatation or dilating element 12. At the proximal ends 19, 19a, 19b there are mounted in conventional manner hose connections. The end 19a is connected by a pressure measuring device M with a suction-pressure pump $Q_P$. Suction-pressure pump $Q_P$ advantageously may be of the type disclosed in the commonly assigned United States application Ser. No. 853,189, filed Nov. 21, 1977, entitled "Clinically Usable Pump Apparatus For A Dilatation Device", to which reference may be had and the disclosure of which is incorporated herein by reference. The further proximal end 19b is likewise connected by a standard hose connection through the intermediary of a roller pump R or other suitable type pump with a blood reservoir $Q_B$.

Now by referring to FIG. 2 there will be apparent the construction of the dilatation or dilating element 12 which has been schematically shown in FIG. 1a. Located upon the double lumen support hose 11 is a transparent hollow cylinder 50 having a wall 13 of substantially cylindrical configuration at the ends of which there are present the substantially conical-shaped wall portions 14 and 14' with which merge the substantially cylindrical-shaped collars 15 and 15', respectively. These cylindrical-shaped collars 15 and 15' enclose the support hose 11 and are connected therewith in a pressure-tight fashion by means of the circumferentially extending adhesive bonds 22. At the distal end 12a of the dilatation element 12 there is arranged a flexible tip 18. At the outer or jacket surface 11a of the support hose 11 there is arranged at the region of its distal end 11b a circular-shaped opening 17 and internally of the dilatation element 12 there is provided a substantially slot-shaped further opening 16 which extends over the length of the wall 13.

By means of the suction-pressure pump $Q_P$ there is delivered to the double lumen support or carrier hose 11 a mixture at a pressure P' consisting of NaCl and a contrast agent furnished by a supply device or reservoir 21. This mixture arrives by means of the opening 16 within the dilatation element 12 and dilates such dilatation element. The degree of dilatation is determined, on the one hand, by the pre-formed dilatation element 12 and, on the other hand, can be controlled within the most narrow limits by the pressure measuring device M, typically a manometer.

By producing a negative pressure in the suction-pressure pump Q_P, which likewise can be controlled at the pressure measuring device M, it is possible to evacuate the dilatation element 12, and thus, with reduced outside diameter to insert such further into the hollow space or cavity which is to be dilated. The flexible tip 18 of the dilatation element 12 is advantageously fabricated from a spring steel wire and serves for the detection of even the smallest passages in the hollow space or cavity which is to be dilated. Since in its dilated state the dilatation element 12 obstructs the throughflow of liquid, it is equally suitable for sealing hollow spaces, and nonetheless it is possible to infeed blood or a contrast agent by means of the opening 17 of the dilatation element 12. Both of the lumens 60 and 61 are separated from one another by one of the adhesive bonds 22 (cf. FIG. 2).

Continuing, in FIG. 3 there is illustrated a pre-formed guide catheter 1' which enables insertion of the dilatation element 12 into the right coronary artery of a human. The inner hose 2', formed of "TEFLON", is brought into its desired form or shape by thermal action. The surface layer for manual control of the catheter arrangement has been designated by reference character 3'.

For the recanalization of coronary arteries at the left side there are employed the guide catheters 1", 1''' of the embodiments shown in FIGS. 4 and 5. The inner hoses 2" and 2''' as well as the surface layers 3" and 3''' are constructed analogous to the showing of FIG. 3.

The construction of the guide catheter, such as used in the arrangement of FIG. 1, will be apparent from the showing of FIG. 6. A synthetic fiber fabric 4 consisting of nylon is tightly woven around the inner hose 2 and such synthetic fiber fabric 4 is form-lockingly covered by a protective layer 5. At the protective layer 5 there has found to be useful a shrink-fitted hose formed of polyvinylchloride. The synthetic fiber fabric 4 and the protective layer 5 collectively constitute a rigid surface layer 3 suitable for the transmission of torsional forces.

The dilatation element 12' shown in FIG. 7 is depicted in its evacuated state. The wall 13' thereof has been schematically shown folded together at the left and right at the locations 13'a and 13'b. With this variant construction the support or carrier hose 11' has a central opening 11'a, whereas at its outer surface there is formed the second lumen serving for dilatation which here is in the form of a groove 16 and tightly covered by an outer hose, which hose, if the section of FIG. 7 were taken at another location through the hose, would appear like the marking element 20 immediately hereinafter mentioned. There also will be recognized a substantially ring-shaped marking element 20 which is fabricated from a gold foil and serves for X-ray localization.

In FIG. 8 there is illustrated the dilatation element 12' of FIG. 7 in its dilated state. As a matter of convenience the same parts or elements have again been designated with the same reference characters.

Once again for dilation there is used a non-compressible medium, preferably a physiological salt solution and/or an X-ray contrast agent, which even in the event of damage to the dilatation element 12' and the therewith resulting flowing-out of such medium into the human body, cannot cause any damage.

With the fabrication of the catheter arrangement, a commercially available adhesive marketed under the trademark "CYANOLIT" by the well-known firm Minnesota Mining and Manufacturing Corporation has been found to be suitable for connecting the individual parts which are extensively formed of plastics.

Catheter arrangements, designed according to the teachings of the present invention, have been employed with dilatation pressures, up to 8 atmospheres excess pressure. Equally, there has been employed without any problem a test pressure exceeding 10 atmospheres excess pressure.

While there are shown and described present preferred embodiments of the invention, it is to be distinctly understood that the invention is not limited thereto, but may be otherwise variously embodied and practiced within the scope of the following claims.
ACCORDINGLY,

What we claim is:

1. A catheter arrangement for opening or closing hollow cavities and the like, comprising:
   a guide catheter;
   a dilatation catheter co-operating with said guide catheter;
   a dilatation element arranged at said dilatation catheter;
   said dilatation element being structured to have two lumens;
   one of said lumens being in flow communication with the exterior of the dilatation element for infeeding a liquid into the hollow cavity;
   the other of said lumens serving for dilating said dilatation element;
   said dilatation element having an at least partially cylindrical, pre-shaped foldable wall expansible to essentially a predetermined limited diameter and defining at least part of a boundary wall of said other lumen.

2. The catheter arrangement as defined in claim 1, wherein:
   the length dimension of the wall amounts to at least twice its outside diameter when the dilatation element is exposed to an internal excess pressure.

3. The catheter arrangement as defined in claim 2, wherein:
   said dilatation element has opposite end regions; and
   each of said opposite end regions of said dilatation element having a substantially coneshaped configuration merging with a substantially cylindrical-shaped collar.

4. The catheter arrangement as defined in claim 2, wherein:
   said dilatation element is formed of polyvinylchloride.

5. The catheter arrangement as defined in claim 2, wherein:
   said dilatation element has a wall thickness amounting to at least 0.01 mm to at most 0.8 mm.

6. The catheter arrangement as defined in claim 2, further including:
   a carrier hose provided for the dilatation catheter;
   said dilatation catheter having a proximal end;
   said carrier hose being provided with a number of hollow spaces defining said lumens which are closed towards one another and communicating with said proximal end of said catheter;
   said catheter having an outer surface; and said hollow spaces opening into the outer surface of said catheter.

7. The catheter arrangement as defined in claim 2, further including:
a carrier hose provided for the dilatation catheter;
said dilatation catheter having a distal region and a proximal end;
said carrier hose being provided with a number of hollow spaces defining said lumens which are closed towards one another and communicating with said proximal end of said catheter and opening into the proximal region of said catheter.

8. The catheter arrangement as defined in claim 2, further including:
an at most slightly radiation-pervious marking element provided at least at the region of the dilatation element for X-ray localization.

9. The catheter arrangement as defined in claim 2, further including:
a radiation-impervious marking element provided at least at the region of the dilatation element for X-ray localization.

10. The catheter arrangement as defined in claim 1, wherein:
said guide catheter comprises an inner hose having an outer surface and a surface layer extending at least over a portion of the length of said inner hose upon its outer surface; and
said surface layer being structured to transmit greater torsional forces in comparison to said inner hose.

11. The catheter arrangement as defined in claim 10, wherein:
said guide catheter has a distal region which is pre-formed in such a manner that it possesses a mechanical pre-stress in relation to its position of use.

12. The catheter arrangement as defined in claim 10, wherein:
said surface layer comprises a synthetic fiber fabric having a protective layer applied thereto.

13. The catheter arrangement as defined in claim 12, wherein:
said synthetic fiber fabric is formed of polyamide and said protective layer of fluoroethylenepropylene.

14. The catheter arrangement as defined in claim 1, wherein:
said two lumens are separate and in non-flow communicating relation to one another.

15. The catheter arrangement as defined in claim 1, further including:
means for infeeding liquid to both of said lumens.

16. A catheter arrangement for opening or closing hollow cavities and the like, comprising:
a guide catheter;
a dilatation catheter co-operating with said guide catheter;
a dilatation element arranged at said dilatation catheter;
said dilatation element having an at least partially cylindrical, foldable wall;
said guide catheter comprising an inner hose having an outer surface and a surface layer extending at least over a portion of the length of said inner hose upon its outer surface;
said surface layer being structured to transmit greater torsional forces in comparison to said inner hose;
said guide catheter having a distal region which is pre-formed in such a manner that it possesses a mechanical pre-stress in relation to its position of use; and
the maximum outer diameter of the guide catheter amounts to approximately two-fold to four-fold its inner diameter and is reduced in size by about 10% to 25% at the pre-formed distal region.

17. A catheterization method employing a catheter arrangement comprising a dilatation catheter and a guide catheter having a bore for receiving the dilatation catheter, comprising the steps of:
introducing the guide catheter by forces acting in translatory and rotational direction and engaging at a surface layer thereof into the near region of a hollow cavity which is to be opened or closed;
then displacing the dilatation catheter which contains a dilatation element having a pre-shaped foldable wall expansible to essentially a predetermined limited diameter and two lumens which are closed towards one another through the bore of the guide catheter, while the dilatation element has an internal space thereof at a negative pressure in relation to the pressure of the hollow cavity which is to be opened or closed;
thereafter displacing the dilatation catheter through the guide catheter to such an extent that the dilatation element arrives at the location which is to be opened or closed;
introducing a liquid into one of the lumens to dilate said dilatation element to a predetermined shape and a predetermined limited diameter at said location by applying a pre-selected excess pressure; and
introducing a liquid into the other lumen for outflow into said hollow cavity.

* * * * *

Disclaimer 4,195,637.—*Andreas Gruntzig* and *Hans Gleichner,* Zurich, Switzerland. CATHETER ARRANGEMENT, METHOD OF CATHETERIZATION, AND METHOD OF MANUFACTURING A DILATATION ELEMENT. Patent dated Apr. 1, 1980. Disclaimer filed Apr. 16, 1981, by the assignee, *Schneider Medintag AG.*

Hereby enters this disclaimer to claims 1 to 17 inclusive of said patent.
[*Official Gazette July 14, 1981.*]